(12) United States Patent
Sparks et al.

(10) Patent No.: US 7,354,429 B2
(45) Date of Patent: Apr. 8, 2008

(54) DEVICE AND METHOD FOR DETECTING AND TREATING CHEMICAL AND BIOLOGICAL AGENTS

(75) Inventors: Douglas Ray Sparks, Whitmore Lake, MI (US); Nader Najafi, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 345 days.

(21) Appl. No.: 10/709,782

(22) Filed: May 27, 2004

(65) Prior Publication Data

US 2008/0065050 A1 Mar. 13, 2008

Related U.S. Application Data

(60) Provisional application No. 60/473,383, filed on May 27, 2003.

(51) Int. Cl.
*A61M 31/00* (2006.01)
*G01N 33/48* (2006.01)

(52) U.S. Cl. ..................... 604/503; 422/68.1
(58) Field of Classification Search ............ 604/93.01, 604/181, 890.1, 891.1, 500, 131, 503, 65–67; 600/309, 362; 422/68.1, 69, 82.01, 88; 436/178, 436/149–151
See application file for complete search history.

(56) References Cited

U.S. PATENT DOCUMENTS

| | | | | |
|---|---|---|---|---|
| 6,887,202 | B2* | 5/2005 | Currie et al. | ............... 600/309 |
| 6,932,114 | B2* | 8/2005 | Sparks | ....................... 137/814 |
| 2003/0191402 | A1* | 10/2003 | Arzbaecher et al. | ........ 600/509 |
| 2004/0158232 | A1* | 8/2004 | Schetky et al. | .......... 604/890.1 |
| 2004/0193025 | A1* | 9/2004 | Steil et al. | ................... 600/316 |

* cited by examiner

*Primary Examiner*—Kevin C. Sirmons
*Assistant Examiner*—Catherine N. Witczak
(74) *Attorney, Agent, or Firm*—Hartman & Hartman, P.C.; Gary M. Hartman; Domenica N. S. Hartman

(57) ABSTRACT

A device and method capable of sensing the presence of biochem agents, and preferably also capable of delivering precise amounts of one or more antidotes to treat a victim exposed to the agents. The device includes a freestanding tube portion having an internal passage containing a substance selective to a chemical or biological agent so that matter accumulates within the freestanding tube portion when a fluid drawn through the tube portion contains the agent. When vibrated at resonance, the resonant frequency of the tube portion is indicative of the accumulation of matter and thereby the presence of the agent to which the substance is selective. The device then preferably delivers precise amounts of one or more appropriate antidotes to treat the victim. The device is a sufficiently small and lightweight unit to permit being carried by an individual.

40 Claims, 2 Drawing Sheets

DEVICE AND METHOD FOR DETECTING AND TREATING CHEMICAL AND BIOLOGICAL AGENTS

CROSS REFERENCE TO RELATED APPLICATIONS

This application claims the benefit of U.S. Provisional Application No. 60/473,383, filed May 27, 2003.

BACKGROUND OF INVENTION

1. Field of the Invention

The present invention generally relates to fluid handling devices, their uses and operation. More particularly, this invention relates to a fluid handling device and method for sensing chemical and biological agents and preferably also treating a person exposed to such agents.

2. Description of the Related Art

The threat of biological and chemical (biochem) attack from terrorists and rogue states has increased in recent years. Biochem threats particularly put military personnel, law enforcement, emergency response, first responders, and postal workers at risk. While not all biochem agents have antidotes, a significant percentage does. For example, antidotes and treatments exist for sarin, VX, tabun, soman, cyanide, lewisite (β-chlorovinyldichloroarsine), anthrax, brucellosis, bubonic plague, Q fever, and botulism.

Biochemical and chemical compounds can be detected through the use of absorption. For example, film materials capable of selectively absorbing certain compounds find use in humidity, pH, glucose, bacteria, blood, cellular, pollution, poisons, gas and biotoxin sensors and detectors. However, many biochem agents that might be used in an attack require immediate treatment to save the victim's life, with the medical response time making the difference between complete recovery and a permanent handicap or death. Making treatment available in the field and in time to be effectively used is desirable but difficult. Treatment on a remote battlefield, especially when fast-acting chemical agents are involved, can be particularly difficult since many affected personnel may be incapacitated. Commercial or military products or systems do not exist that can provide immediate and effective defense against an actual biochem attack.

In view of the above, it would be desirable if a portable rapid-response device were available as a first defense for individuals against chemical and biological terrorist attacks. Such a device would preferably be capable of detecting the type and amount of biochem agent. Such a device would also be preferably capable of selecting one or more appropriate antidotes, and precisely delivering appropriate amounts and concentrations of antidote(s) to the victim. Finally, it would be advantageous if the number of separate components required to perform these functions could be minimized while maintaining or improving the precision by which these functions are performed.

SUMMARY OF INVENTION

The present invention provides a device and method capable of sensing the presence of biochem agents, and also preferably delivering precise amounts of one or more antidotes to treat a victim exposed to the agents.

According to one aspect of the invention, a device capable of detecting a chemical or biological agent includes a freestanding tube portion comprising an internal passage containing a substance selective to a chemical or biological agent so that matter accumulates within the freestanding tube portion. The device further includes means for flowing a fluidic sample through the freestanding tube portion, means for vibrating the freestanding tube portion at a resonant frequency thereof that varies with the combined density of the freestanding tube portion and any contents of its internal passage, means for sensing movement of the freestanding tube portion and producing an output signal based on the resonant frequency of the freestanding tube portion and indicative of accumulation of matter, and means for identifying the agent in the fluidic sample based on the accumulation of matter in the freestanding tube portion.

In view of the above, a method performed by the detecting device involves detecting a chemical or biological agent by flowing a fluidic sample through a freestanding tube portion having an internal passage containing a substance selective to a chemical or biological agent so that matter accumulates within the freestanding tube portion, vibrating the tube portion at a resonant frequency thereof that varies with the combined density of the freestanding tube portion and contents of the internal passage, sensing movement of the freestanding tube portion to produce an output signal based on the resonant frequency of the freestanding tube portion and indicative of accumulation of the reaction product, and identifying the agent in the fluidic sample based on the accumulation of the reaction product in the freestanding tube portion.

According to a second aspect of the invention, the detecting device is preferably used in combination with a device capable of delivering precise amounts of one or more antidotes to treat a victim that has been exposed to the biochem agents detected by the detecting device of this invention. The delivery device comprises a unit sufficiently small and lightweight to be carried by a person. The delivery device includes at least one antidote, means coupled to the at least one antidote for selecting the at least one antidote, means for delivering the at least one antidote into the body of the person, and means for communication between the selecting means and the delivering means. The detecting device preferably communicates with the selecting means of the delivery device and identifies the antidote(s) capable of counteracting the detected agent for the delivery device.

In a preferred embodiment of the invention, each of the detecting and delivery devices makes use of a micromachined resonating tube of a type disclosed in U.S. Pat. No. 6,477,901 to Tadigadapa et al. According to Tadigadapa et al., a resonating tube is operated on the basis of the Coriolis effect to sense mass flow and density of a flowing fluid. In the present invention, a resonating tube is adapted to sense a change in the mass of the tube as a result of the matter that accumulates as a result of the presence of a chemical or biological agent drawn through the tube.

The detecting and delivery devices described above are capable of being miniaturized and combined in a sufficiently small package to permit carrying by a person. As such, the devices are capable of being essential components of a portable rapid-response unit suitable for use as the first defense for individuals against chemical and biological attack. When used together, the detecting and delivery devices are capable of detecting the type and amount of biochem agent present, and then selecting and precisely delivering appropriate amounts and concentrations of the appropriate antidote(s) to the victim.

Other objects and advantages of this invention will be better appreciated from the following detailed description.

DETAILED DESCRIPTION

Figure 1:
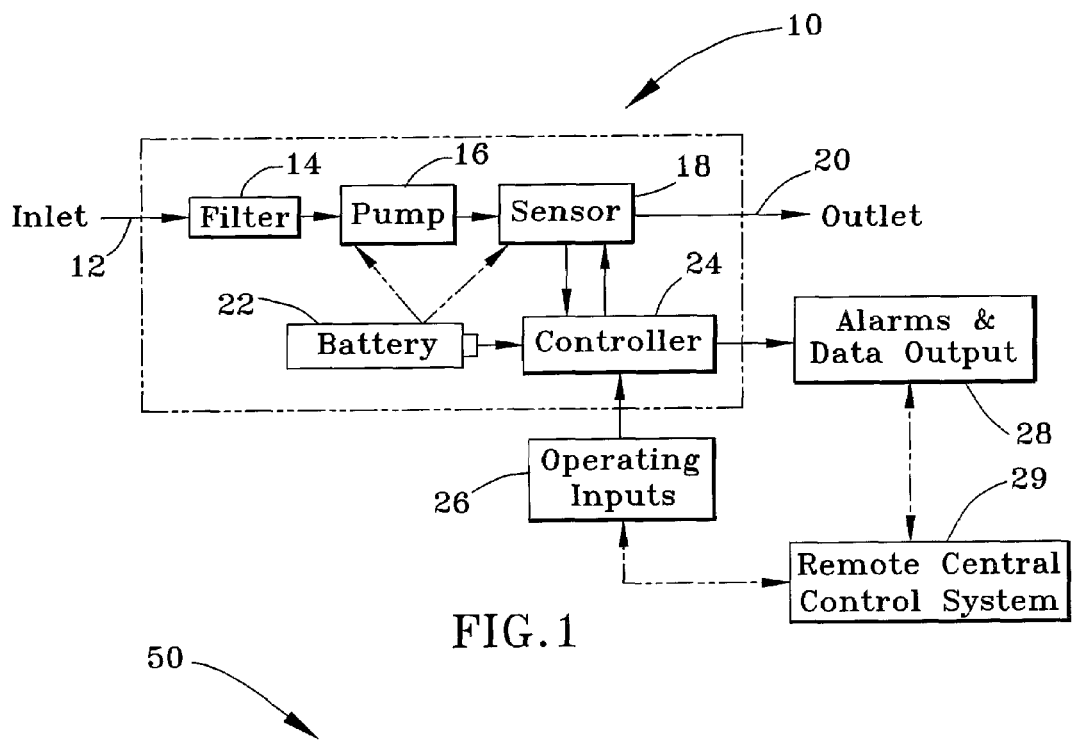
FIG. 1 is a schematic of a device capable of detecting a chemical or biological agent in accordance with a first aspect of this invention.
Figure 2:
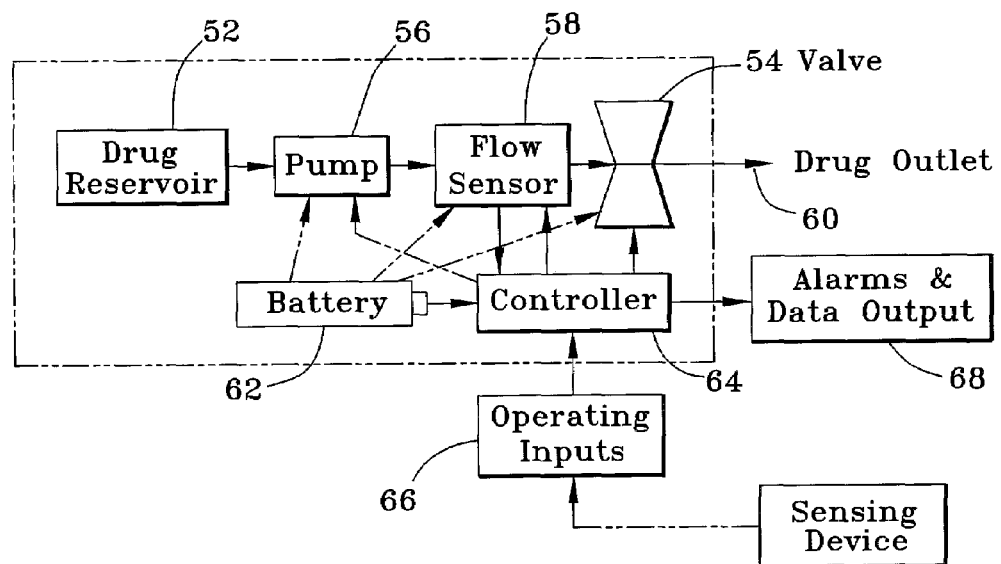
FIG. 2 is a schematic of a device capable of delivering an antidote for a chemical or biological agent in accordance with a second aspect of this invention.

With reference to FIGS. 1 and 2, two devices 10 and 50 are shown that, separately or in combination, are capable of detecting a chemical or biological (biochem) agent and delivering an antidote or other appropriate treatment for the biochem agent, respectively. The devices 10 and 50 are preferably miniaturized units that are sufficiently small and lightweight to be combined in a single unit that can be carried by a person, especially those susceptible to attack with a biochem agent. Each device 10 and 50 makes use of a flow sensor 18 and 58, respectively, of a type that makes miniaturization of the devices 10 and 50 possible. In preferred embodiments of the invention, each flow sensor 18 and 58 contains one or more micromachined resonating tubes capable of measuring certain properties of a fluid using Coriolis force principles. A preferred flow sensor of this type is taught in U.S. Pat. No. 6,477,901 to Tadigadapa et al., incorporated herein by reference.

Figure 4:
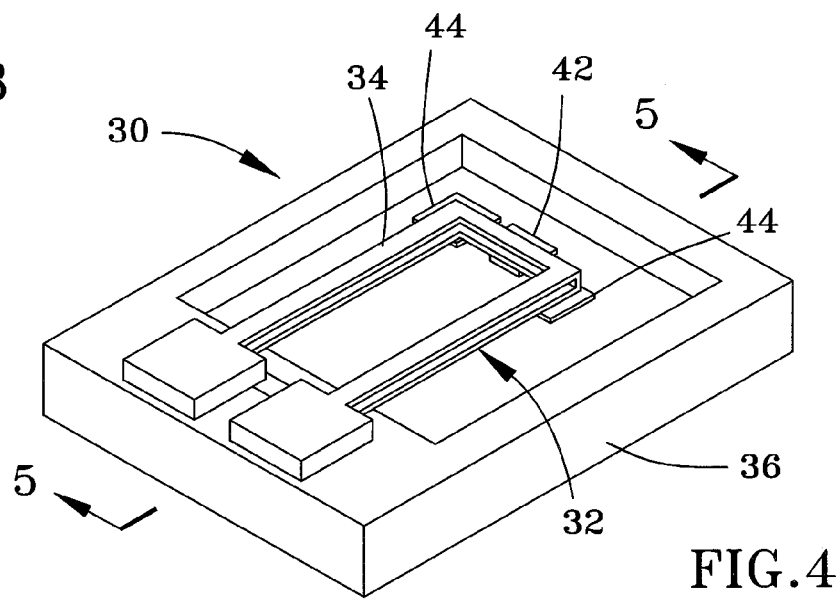
FIGS. 4 and 5 represent a micromachined resonating tube suitable for use in the devices of FIGS. 1 and 2.
Figure 5:
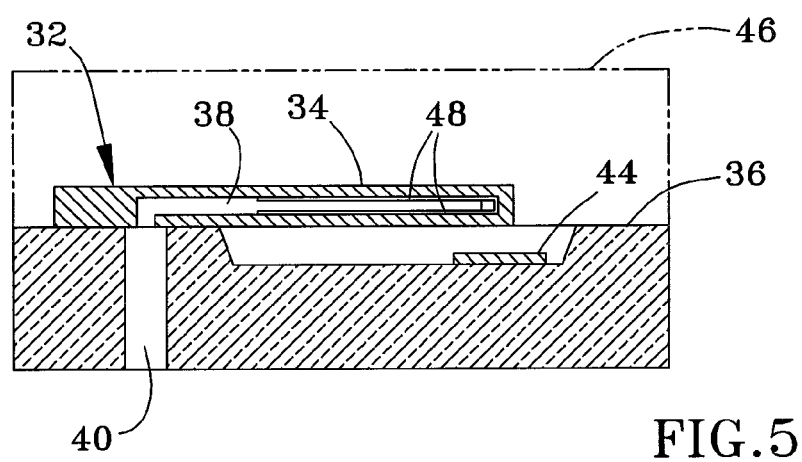

A flow sensor 30 in accordance with Tadigadapa et al. and suitable for use in or as the flow sensors 18 and 58 is represented in FIGS. 4 and 5. Briefly, the sensor 30 is depicted as having a single micromachined resonating tube 32 fabricated on a substrate 36, though any number of resonating tubes 32 could be fabricated on the substrate 36 and/or on any additional number of substrates. According to Tadigadapa et al., the flow sensor 30 represented in FIGS. 4 and 5 can be used to measure the flow rate of a fluid flowing through a freestanding portion 34 of its tube 32 by sensing the degree to which the freestanding portion 34 deflects (twists) when vibrated, and can be used to measure the density of the fluid by sensing changes in the resonant frequency of the freestanding portion 34. When packaged in a vacuum, the sensor 30 is capable of producing a high Q signal. Furthermore, the resonating tube 32 can be miniaturized by micromachining techniques to hold just a few nanoliters of fluid (1 to 1000 nL). As such, the resonating tube 32 represented in FIGS. 4 and 5 is ideally suited for use with the small, lightweight devices 10 and 50 of FIGS. 1 and 2, and the devices 10 and 50 will be described as using sensors 18 and 58 that make use of such tubes 32. However, it is foreseeable that other miniaturized fluid-handling devices could be developed by which biochem agents can be detected and the appropriate antidote(s) delivered in accordance with this invention.

The device 10 depicted in FIG. 1 is adapted for detecting the presence of a biochem agent, and preferably the type and concentration of the agent in a fluid being sampled. The fluid may be any liquid or gas through which a biochem may be delivered, such as air, water, biological fluids, as well as fluids in which a biochem agent may be detected in a victim, such as the victim's blood or urine. The detecting device 10 is represented as including an inlet 12, a filter 14, a pump 16 that operates to draw the fluid into the device 10, the above-noted flow sensor 18, and an outlet 20 through which the fluid exits the device 10. The pump 16 is a suitable miniaturized fan or pump capable of moving the fluid intended for analysis. Alternatively, some applications may allow the fluid to be injected into the device 10 with a syringe or pipette (not shown). The filter 14 upstream of the pump 16 and sensor 18 is desirable and may be necessary to protect the sensor 18 from clogging or to assist in separating elements of the fluid, for example, separating white from red blood cells. Accordingly, the type of filter 14 employed by the device 10 will depend on the type of fluid being analyzed.

As discussed above, the sensor 18 preferably employs one or more micromachined resonating tubes 32 of the type disclosed in Tadigadapa et al. As used herein, micromachining is a technique for forming very small elements by bulk etching a substrate (e.g., a silicon wafer), or by surface thin-film etching, the latter of which generally involves depositing a thin film (e.g., polysilicon or metal) on a sacrificial layer (e.g., oxide layer) on a substrate surface and then selectively removing portions of the sacrificial layer to free the deposited thin film. Accordingly, suitable materials for the tube 32 include glass (e.g., quartz and Pyrex), ceramic, metal or a semiconductor, including micromachined silicon, germanium, Si/Ge and GaAs. FIGS. 4 and 5 show a suitable configuration for the tube 32 having a pair of legs and an interconnecting cross-member, yielding essentially a U-shaped freestanding tube portion 34 suspended above the surface of the substrate 36. While a U-shaped freestanding tube portion 34 is shown, other shapes—both simpler and more complex—are within the scope of this invention. The tube portion 34 defines a continuous fluid passage 38 between an inlet and outlet 40 located on the opposite surface of the substrate 36. As previously noted, micromachining technologies employed to fabricate the tube 32 enable the size of the tube 32 and its passage 38 to be extremely small, such as lengths of about 0.5 mm and cross-sectional areas of about 100 $\mu m^2$, enabling the device 10 to process very small quantities of fluid.

The freestanding tube portion 34 is preferably driven at resonance, with the resonant frequency being determined in part by its mechanical design (shape, size, construction and materials). Suitable frequencies are in the range of 1 kHz to over 100 kHz, depending on the particular fluid being analyzed. Under most circumstances, frequencies above 10 kHz, including ultrasonic frequencies (those in excess of 20 kHz), will be preferred. The amplitude of vibration is preferably adjusted through means used to vibrate the tube portion 34. For this purpose, FIG. 4 shows an electrode 42 located beneath the tube portion 34 on the surface of the substrate 36. In the embodiment shown, the tube 32 serves as an electrode (e.g., is formed of doped silicon) that is capacitively coupled to the electrode 42, enabling the electrode 42 to electrostatically drive the tube portion 34. However, it is foreseeable that the tube 32 could be formed of a non-conductive material, and a separate electrode formed on the tube portion 34 opposite the electrode 42 for vibrating the tube portion 34 electrostatically. Furthermore, the tube portion 34 could be driven capacitively, piezoelectrically, piezoresistively, acoustically, ultrasonically, magnetically, optically, or by another actuation technique. Also shown in FIGS. 4 and 5 are sensing elements 44 for providing feedback to enable the vibration frequency and amplitude to be controlled with appropriate circuitry of a controller 24, which may be located on the substrate 36 or on a separate substrate. While capacitive sensing is preferred, the sensing elements 44 could sense the proximity and motion of the tube portion 34 in any other suitable manner.

FIG. 5 schematically represents the micromachined tube 32 as being enclosed by a cap 46 bonded or otherwise attached to the substrate 36. In a preferred embodiment, the bond between the cap 46 and substrate 36 is hermetic, and the resulting enclosure formed between the substrate 36 and cap 46 is evacuated to enable the tube portion 34 to be driven efficiently at high Q values without damping. A suitable material for the cap 46 is silicon, allowing silicon-to-silicon bonding techniques to be used, though other cap materials and bonding techniques are possible and within the scope of the invention.

In Tadigadapa et al., monitoring the frequency of vibration of the tube portion 34 while a fluid flows through the passage 38 enables the density and mass flow rate of the fluid to be measured. As fluid flows through the tube portion 34 while the tube portion 34 is vibrated at resonance, the tube portion 34 twists under the influence of the Coriolis effect. As explained in Tadigadapa et al., the degree to which the tube portion 34 twists (deflects) when vibrated can be correlated to the mass flow rate of the fluid flowing through the tube portion 34 on the basis of the change in the amplitude of a secondary resonant vibration mode. The density of the fluid is proportional to the natural frequency of the fluid-filled vibrating tube portion 34, such that controlling the vibration of the tube portion 34 to maintain a frequency at or near its resonant frequency will result in the vibration frequency changing if the density of the fluid flowing through the tube portion 34 changes.

In contrast to Tadigadapa et al., the detecting device 10 of FIG. 1 is not particularly concerned with the mass flow rate of a fluid through the tube portion 34, but instead is interested in a change in mass that will occur over time during operation of the device 10 if the fluid being sampled contains a biochem agent. For this purpose, one or more interior wall surfaces of the tube portion 34 is coated or filled with a substance that absorbs, chemically reacts with, biologically reacts with, or otherwise causes the accumulation of matter when a specified biochem agent is present in the fluid flowing through the tube 32. Such a substance is depicted in FIG. 2 as a film 48, hereinafter the accumulation film 48, though it is to be understood that the film 48 could be a porous material that substantially fills the passage 38, and the term "accumulation" is intended to encompass absorption, reactions, and any other mechanism that causes matter (e.g., the biochem agent, a reaction product thereof, etc.), to accumulate within the tube portion 34. As accumulation takes place, the mass of the resonant tube portion 34 also changes, generally increasing though possibly decreasing, depending on the relative densities of the fluid, the biochem agent, and the matter that accumulates in the tube portion 34. The mass change causes a resonant frequency change in the tube portion 34, enabling the sensor 18 to operate as a microscale that can be selective to a given chemical or biological agent. The sensor 18 can be fabricated to contain any number of tubes 32, each dedicated to sensing the presence of a different biochem agent through the use of different substances for the films 48 within the tubes 32. In this manner, a change sensed in the resonant frequency of a particular tube 32 can be immediately recognized by the device 10 as indicating the presence in the sampled fluid of the agent for which the film 48 within the tube 32 is selective. The rate at which the resonant frequency of a tube 32 changes is also potentially of interest as indicating the concentration of the agent in the sampled fluid. For this purpose, the controller 24 can include clock circuitry against which changes in resonant frequency (corresponding to accumulation of matter within the tube 32 and therefore the presence of agents in the sampled fluid) can be monitored.

The detecting device 10 has application for detecting the presence of a wide variety of biochemical agents, including chemical warfare agents (mustard gas, cyanide, lewisite, nerve agents, etc.) and biological warfare agents (anthrax, botulism, Brucellosis, plague, Q-fever, etc.). The device 10 can also be employed to detect a variety of other potentially harmful agents, including a variety of bacteria and viruses, dust, soot, organic solvents, drugs, explosive elements, poisons, gases, biotoxins, tainted food, water and air pollution, as well as the presence and/or properties of other chemicals, compounds, and particles of potential interest, such as humidity, pH, glucose, blood and its components, antibodies, cells, enzymes, DNA, proteins, white blood cells, urine and its components, etc. If bacteria detection is desired, the device 10 may require the capability of accumulating and incubating enough cells in the tube 32 for detection. However, since the tube 32 can be fabricated to have a volume of only several nanoliters, the invention offers the advantage of being able to detect the presence of a bacteria with only a few cells.

Liquid and gaseous deposition techniques can be employed to deposit the film 48, such as by injecting the absorbent or chemically/biologically reactive material into the tube 32 and allowing the material to dry to form the accumulation film 48. The performance of the tube 32 formed by silicon micromachining can be enhanced with several fabrication and design techniques. For example, single or multiple layers can be deposited or formed on the inner surfaces of the tube passage 38 to provide a surface that is more chemically reactive than the material of which the tube 32 is formed, for example, silicon or silicon oxide. For example, a metal such as gold can be deposited and then coated with a film 48 formed by a layer of thiolated single-stranded DNA to detect complementary DNA strands. Furthermore, platinum has been shown to attract proteins. Metal suicides can be deposited to improve adhesion of platinum and other reactive metals to a silicon tube 32. Furthermore, one or more polymer layers can be applied before application of a reaction-promoting layer (if present) and the film 48 to promote adhesion of these layers to tube surfaces formed of silicon, silicon oxide, silicon nitride, metal, metal silicide, etc.

The sensitivity of the tube portion 34 to mass change generally increases as the thickness of the film 48 increases relative to the tube wall thickness. Therefore, a relatively thick film 48 and/or relatively thin tube walls are generally desirable. For the latter, the tube 32 can be isotropically thinned with a plasma or wet etch after release of the tube portion 34 during the fabrication process. Nano-technology can also be used for the fabrication of the tube 32 to further increase the sensitivity of the sensor 30.

Since the densities of materials vary with temperature, temperature control is often used to manufacture highly accurate density meters of the prior art, such as thermoelectrically-controlled resonant temperature systems. Because the densities of the tube material, coatings, and analyzed fluids are all subject to change with temperature, the controller 24 may include a temperature control element (not shown) to sense the temperature of the flow sensor 18 and thereby achieve higher accuracy of chemical and biological detection with the device 10. Temperature control can also be used to improve the performance and reduce the damage to biologic compounds. As represented in FIG. 1, the controller 24 preferably controls the pump 16, the sensor 18 and its resonating tube portion 34, and any temperature or other compensating devices. Furthermore, these devices are shown as being powered by an on-board battery 22 or other power storage device. Suitable devices for this purpose are known and therefore will not be discussed in any detail here.

As noted above, the sensor 18 can comprise arrays of the flow sensor 30 depicted in FIGS. 4 and 5, which in turn may comprise any number of resonating tubes 32. By providing multiple tubes 32 with different absorbent/reactive films 48, the device 10 is capable of detecting many different chemicals, cells and/or biotoxins. Multiple sensors 18 and digital logic with memory can be employed to reduce the incidence of false positive chemical identifications occurring. Operating inputs 26 to the controller 24 and alarms and data output 28 from the controller 24 enable the device 10 in be used as a stand-alone unit carried by an individual for personal protection from biochem agents, or used as a unit for wireless communication with a remote central control system 29. In the latter embodiment, the device 10 can perform widely dispersed environmental monitoring or be used as a medical implant to check on internal chemical activity within the individual. As such, the invention is capable of continuous monitoring of air and water surrounding an individual carrying the device 10, or can be implanted in an individual to continuously monitor urine, blood, or other bodily fluids, or placed in various other environments to monitor the presence of agents within air systems, water systems, industrial chemicals, etc.

A significant advantage of the invention is that, because of the miniaturized sensor 18, the detecting device 10 can be small, portable and relatively inexpensive, especially when fabricated by micromachining technology to yield what is known as a microelectromechanical system (MEMS). It is foreseeable that the cost of the device 10 can be sufficiently low to render the device 10 disposable. Alternatively, the sensor 18 can be recycled after the film 48 becomes saturated. For example, heat and/or an aggressive detergent or solvent could be flushed through the tube 32 to strip the inner walls of the film 48 and the matter that has accumulated within the tube 32 as a result of absorption and/or reaction with a biochem agent. After cleaning, the inner walls of the tube 32 can be recoated if needed or desired. In view of the above, device size, batch fabrication and recycling can all contribute to reducing the cost of sensing biochem agents with the device 10.

In an investigation leading up to the invention, water was injected into a flow sensor of the type represented in FIGS. 4 and 5. In response, the resonant frequency of the tube dropped from about 11 KHz to about 8.6 KHz. After removing the water with compressed air, the frequency initially increased to about 10.950 KHz and then gradually continued to rise, indicating that a film of water remained on the inside of the tube. In view of this observation, it was evident that the sensor was capable of sensing the presence of a very fine film that had accumulated within the tube after flow had been discontinued and the bulk of the water removed. Heating the tube and pulling a vacuum inside the tube eventually restored the resonant frequency of the tube to the original 11 KHz. Similar sensitivities to the accumulation of other materials have also been observed, such as when testing oils. From these observations, it was concluded that the inner surfaces of a resonating tube could be manufactured to intentionally and selectively absorb agents (e.g., biochem agents) to enable the device to operate as a sensor or microscale for such agents.

As previously noted, the delivery device 50 represented in FIG. 2 is adapted for delivering an antidote or other appropriate treatment to an individual, such as through a needle (not shown) or other device capable of delivering an antidote in an appropriate manner. Notable examples include a subdermal patch or intramuscularly (IM) or intravenously (IV) delivery through an IM/IV line, though other delivery methods are possible, e.g., intraarterially, subcutaneously, intraperitoneally or intrathecally. The delivery device 50 is particularly well suited for use in combination with the detecting device 10 of FIG. 1, though the devices 10 and 50 could also be used separately and independently. In combination, the devices 10 and 50 are capable of being part of a single unit that can be carried by a person to sense chemical and biological warfare agents and deliver an appropriate antidote, preferably from an inventory of multiple drugs contained in the device 50.

The device 50 is represented in FIG. 2 as including a reservoir 52 suitable for containing one or more antidotes, a valve 54, a pump 56, the previously-described flow sensor 58, and an outlet 60 through which the antidote exits the device 50 and is delivered to the individual. While the reservoir 52 and pump 56 are represented as separate components, their functions could be combined in a single component, such as by fabricating the reservoir 52 of one or more elastomeric bladders that contain the antidotes under pressure. As with the detecting device 10 of FIG. 1, the delivery device 50 includes a controller 64 that communicates with the flow sensor 58 to control the operation of its resonating tube 32. The controller 64 also preferably communicates with the valve 54 and pump 56 to allow flow through the device 50 to be initiated when treatment is required in response to detection of a harmful agent, and stopped when sufficient antidote has been delivered for the type and amount of agent detected. Also similar to the detecting device 10, the delivery device 50 is equipped with a battery 62 for powering the valve 54, pump 56, flow sensor 58 and controller 64. Furthermore, operating inputs 66 to the controller 64 and alarms and data output 68 from the controller 64 enable the operation of the device 50 to be observed and controlled by the user.

As discussed above, the sensor 18 preferably employs one or more micromachined resonating tubes 32 of the type disclosed in Tadigadapa et al. Resonating tube flow sensors of the type disclosed by Tadigadapa et al. are preferred in view of their very small size and ability to precisely measure extremely small amounts of fluids, in contrast to prior art Coriolis-type flow sensors. For example, if the flow sensor 58 of FIG. 2 employs a resonating tube of the type shown in FIGS. 4 and 5, flow rate measurement accuracies of under +/−1% can be achieved, in contrast to conventional infusion pumps whose accuracies can range from about +/−15% for volumetric pumps down to +/−3% for syringe pumps. While the high cost and the high flow rate requirements for prior art Coriolis-type flow sensors have restricted their use in the drug delivery arena, the flow sensor of Tadigadapa et al. is able to sense the extremely low flow rates (e.g., less than 0.5 ml/hr) that can be necessary when administering an antidote. Another advantage is that use of an electrostatic drive and capacitive sensing (as represented in FIGS. 4 and 5) minimizes the power requirements of the sensor 58. Accordingly, the flow sensor taught by Tadigadapa et al. is ideal for achieving the high dosage accuracy, reliability, small size, biocompatibility, drug compatibility, and low power requirements needed for the device 50 of this invention.

Figure 3:
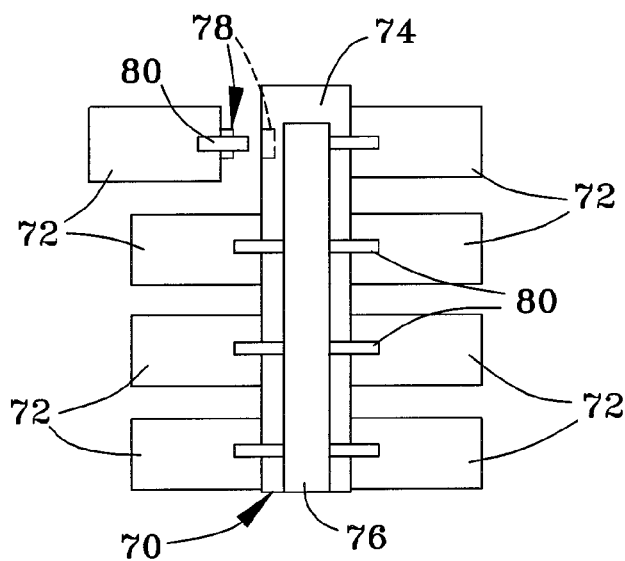
FIG. 3 is a schematic of a multi-antidote manifold for use with the device of FIG. 2.

The reservoir 52 schematically depicted in FIG. 2 can be adapted to contain any number of antidotes or treatments for delivery to the individual. Furthermore, the amounts of these antidotes carried by the device 50 can be very small and concentrated, and therefore very potent, in view of the accuracy of the flow sensor 58. FIG. 3 depicts a manifold system 70 to which a number of cartridges 72 are mounted to provide a multi-antidote infusion system that combines the reservoir 52, valve 54, and sensor 58 of FIG. 2 in a single assembly. The manifold 70 comprises a fluid manifold 74 and an electrical manifold or power bus 76, to which each cartridge 72 is fluidically and electrically connected through connectors 78 and 80, respectively. The manifold system 70 can be fabricated to carry a sensor 58 and valve 54 dedicated to each cartridge 72. Since the manifold system 70 is modular, the sizes of the cartridges 72 can vary to accommodate different dosing requirements. The power bus 76 provides power to the sensors 58 and valves 54, relays input and output signals between the controller 64 (not shown) and the sensors 58, and relays input signals from the controller 64 to the valves 54.

While capable of being configured to have any number of cartridges 72, the manifold system 70 depicted in FIG. 3 is notably equipped with sufficient cartridges 72 to treat the following eleven biochem agents that have antidotes and pose a serious threat in the hands of terrorists and rogue states: sarin, VX, tabun, soman, cyanide, lewisite (ᴲ-chlorovinyldichloroarsine), anthrax, brucellosis, bubonic plague, Q fever, and botulism. The manifold system 70 is shown as being equipped with eight cartridges 72 that can contain atropine and 2-PAM-Cl for nerve agents, botulism antitoxin, tetracycline and doxycycline for the initial treatment of anthrax, brucellosis, Q-fever and the plague, BAL or dimercaprol for lewisite and sodium nitrile followed by sodium thiosulphate for cyanide poisoning. Subsets of these drug combinations or alternate drugs could also be utilized in the manifold system 70.

Delivery of one or more antidotes can be initiated with the controller 64 either through manual input by the user, a radio signal from a remote central location (e.g., the control system 29 of FIG. 1), or in response to one or more detecting devices (e.g., the detecting device 10 of FIG. 1) carried on the person or placed in the local vicinity. The programmability of the device 50 can include, but is not limited to, which antidote or combinations of antidotes should be delivered, the dosage, and the timing of the delivery (e.g. continuous or intermittent) for a variety of treatment regimes. In addition, because antidote dose requirements for many chemical agents are body weight dependant, the programmability of the device 50 also preferably allows the user to preprogram his or her body weight into the device 50 to improve self-treatment and safety.

In addition to the above, the device 50 can be configured to offer other advantages and functions. For example, the ability to measure antidote density can be used to prevent deliver of the wrong antidote or those that are spoiled or contain air bubbles or inclusions. Other functionalities that can be combined with the device 50 include indicating the location of the individual (e.g., through GPS (global positioning system)), broadcasting an alert signal to a remote center or others equipped with similar delivery devices 50 if delivery of an antidote is commenced in response to an attack, monitoring of the individual's biological functions (e.g., heart beat), sending such biological information to a remote center or another individual, etc. Along with the device 50 (including its valve 54, pump 56, sensor 58, and injection device), such additional components can be fabricated by micromachining to yield a fully integrated system that is small, low-power, rugged and biocompatible at high production volumes.

In use, after being notified of the presence of a biochem agent (such as by detection with the detecting device 10), the user can place a needle connected to the device 50 in his or her body and then activate the device 50 to allow the device 50 to deliver the appropriate anti-dote combination and dosage based on the type and concentration of agent sensed. Alternatively, in high risk situations such as a battlefield or suspected contaminated area, a needle or catheter can be pre-inserted so that the device 50 can inject the appropriate antidote combination and dosage without any (or minimal) direct input or action from the user. In one particular example, a remote central detection system (e.g., making use of the detecting device 10) can be linked through a wireless radio network with one or more of the delivery devices 50. When an alert from the central detection system is received, each device 50 automatically selects the appropriate antidote(s) and delivers the antidote(s) at the appropriate dose and delivery timing to the individual wearing the device 50. In another example, each device 50 has a keypad (not shown) to interface with the controller 64. When instructed that exposure to a chemical or biological agent has occurred (e.g., verbally, through a remote central detection system, with the detecting device 10, etc.), the user can punch in the appropriate code to cause the device 50 to select and deliver the correct antidote. In a third example, the detecting device 10 and the delivery device 50 are contained in a single portable unit, so that the unit contains all of the components necessary to sense and automatically respond to a chemical or biological threat.

In view of the above, the present invention provides a biochem detecting device 10 and an antidote delivery device 50 that can be combined into a single unit as a first defense for individuals against a chemical and/or biological attack. In combination, the detecting device 10 and delivery device 50 provide for the automatic detection of the type and amount of biochem agent present, selection of an appropriate antidote combination from multiple reservoirs, preparation and mixing of the appropriate antidotes at the correct concentration, and delivery of such antidote(s) with great accuracy. As such, the invention provides a small, portable, rapid-response bio-protector that can be carried as standard equipment by a soldier or other at-risk personnel for rapid treatment during an attack without the intervention of a medical professional. If the treatment is carried out automatically, the invention has the further advantage of being capable of precise dose control and repeated, timed injections as may be necessary.

While the invention has been described in terms of certain embodiments, it is apparent that other forms could be adopted by one skilled in the art. Therefore, the scope of the invention is to be limited only by the following claims.

The invention claimed is:

1. A device for detecting a chemical or biological agent and treating a person if the person is exposed to the agent, the device comprising:
   a unit sufficiently small and light-weight to be carried by a person, the unit comprising at least one antidote for at least one agent selected from the group consisting of chemical and biological agents, means for selecting the at least one antidote, means for delivering the at least one antidote into the body of the person, and means for communication between the selecting means and the delivering means; and means for detecting the presence of the at least one agent in a fluid sample near the person, the detecting means being in communication with the selecting means and operable to detect the agent in the fluid sample, identify the at least one antidote as being capable of counteracting the agent and if the agent is detected then cause the delivering means to deliver the at least one antidote into the body of the person;

wherein the delivering means comprises:

a tube comprising a freestanding tube portion through which the at least one antidote flows;

means for vibrating the freestanding tube portion of the tube at a resonant frequency thereof that varies with the density of the at least one antidote flowing therethrough, the Coriolis effect causing the freestanding tube portion to twist while being vibrated at resonance, the freestanding tube portion exhibiting a degree of twist that varies with the mass flow rate of the at least one antidote flowing therethrough;

means for sensing movement of the freestanding tube portion of the tube, the movement-sensing means producing a first output signal based on the resonant frequency of the freestanding tube portion and a second output signal based on the degree of twist of the freestanding tube portion;

means for measuring elapsed time during which the at least one antidote has flowed through the tube; and means for stopping flow of the at least one antidote through the tube in response to either of the first and second output signals from the movement-sensing means.

2. The device according to claim 1, wherein the delivering means is operable to deliver the at least one antidote subdermally, intravenously, subcutaneously, or intramuscularly.

3. The device according to claim 1, wherein the unit comprises a plurality of antidotes and the selecting means selects among the plurality of antidotes.

4. The device according to claim 1, wherein the selecting means is operable to select more than one antidote, and the delivering means is operable to deliver the more than one antidote into the body of the person.

5. The device according to claim 1, wherein the detecting means is remote from the unit and not carried by the person.

6. The device according to claim 1, wherein the detecting means is physically coupled to the unit and carried on the person.

7. The device according to claim 1, further comprising means for measuring density of the at least one antidote.

8. The device according to claim 1, further comprising means for sending a signal indicating the location of the person.

9. The device according to claim 1, further comprising means for broadcasting an alert signal to a remote location if delivery of the at least one antidote is commenced.

10. The device according to claim 1, further comprising means for monitoring biological functions of the person, identifying biological information based on the biological functions, and sending the biological information to a remote location.

11. The device according to claim 1, wherein the detecting means comprises a substance that causes accumulation of matter when the agent is present in the fluid sample.

12. The device according to claim 1, wherein the detecting means obtains the fluid sample from the person's surroundings.

13. The method according to claim 12, wherein the fluid sample is air.

14. The method according to claim 12, wherein the fluid sample is water.

15. The device according to claim 1, wherein the detecting means is operable to detect the type of the agent in the fluid sample.

16. The device according to claim 1, wherein the detecting means is operable to detect multiple different agents in the fluid sample and identify multiple antidotes therefor to counteract the multiple different agents.

17. A device for detecting a chemical or biological agent and treating a person if the person is exposed to the agent, the device comprising:

a unit sufficiently small and light-weight to be carried by a person, the unit comprising at least one antidote for at least one agent selected from the group consisting of chemical and biological agents, means for selecting the at least one antidote, means for delivering the at least one antidote into the body of the person, and means for communication between the selecting means and the delivering means; and means for detecting the presence of the at least one agent in a fluid sample near the person, the detecting means being in communication with the selecting means and operable to detect the agent in the fluid sample, identify the at least one antidote as being capable of counteracting the agent and if the agent is detected then cause the delivering means to deliver the at least one antidote into the body of the person;

wherein the detecting means comprises:

a freestanding tube portion through which flows a portion of atmosphere surrounding the person, the freestanding tube portion comprising an internal passage containing a substance selective to the agent so that matter accumulates within the freestanding tube portion;

means for vibrating the freestanding tube portion at a resonant frequency thereof that varies with a combined density of the freestanding tube portion and contents of the internal passage; and means for sensing movement of the freestanding tube portion and producing an output signal based on the resonant frequency of the freestanding tube portion, the output signal being indicative of accumulation of the matter and thereby presence of the agent in the atmosphere surrounding the person.

18. A method of detecting a chemical or biological agent and treating a person if the person is exposed to the agent, the method comprising the steps of:

equipping the person with a unit sufficiently small and light-weight to be carried by the person, the unit comprising at least one antidote for at least one agent selected from the group consisting of chemical and biological agents, means for selecting the at least one antidote, and means for delivering the at least one antidote into the body of the person;

detecting the presence of the at least one agent in a fluid sample near the person;

if the agent is detected, sending a first signal to the selecting means;

selecting with the selecting means the at least one antidote as being capable of counteracting the agent in accordance with the first signal;

sending a second signal to the delivering means; and then delivering with the delivering means the at least one antidote into the body of the person in response to the second signal;

wherein the step of detecting the agent is performed on the person and with the unit, and wherein the step of detecting the agent comprises the steps of:

flowing a portion of atmosphere surrounding the person through an internal passage of a freestanding tube portion, the passage containing a substance selective to the agent so that matter accumulates within the freestanding tube portion;

vibrating the freestanding tube portion at a resonant frequency thereof that varies with a combined density of the freestanding tube portion and contents of the internal passage; and then sensing movement of the freestanding tube portion and producing an output signal based on the resonant frequency of the freestanding tube portion, the output signal being indicative of accumulation of the matter and thereby presence of the agent in the atmosphere surrounding the person.

19. The method according to claim 18, wherein the at least one antidote is delivered subdermally, intravenously, subcutaneously, or intramuscularly.

20. The method according to claim 18, wherein the unit comprises a plurality of antidotes and the selecting means selects among the plurality of antidotes.

21. The method according to claim 18, wherein the selecting step comprises selecting more than one antidote, and the delivering step comprises delivering the more than one antidote into the body of the person.

22. The method according to claim 18, wherein the step of detecting the agent is not performed on the person or with the unit.

23. The method according to claim 18, further comprising inserting the delivery means into the body of the person after the step of detecting the agent.

24. The method according to claim 23, wherein the step of sending the second signal to the delivering means is manually performed by the person.

25. The method according to claim 23, wherein the step of detecting the agent is not performed on the person or with the unit.

26. The method according to claim 18, wherein the step of detecting the agent occurs after inserting the delivering means into the body of the person.

27. The method according to claim 26, wherein the step of detecting the agent is performed on the person and with the unit.

28. The method according to claim 26, wherein the step of detecting the agent is not performed on the person or with the unit.

29. The method according to claim 26, wherein the steps of sending the second signal to the delivering means and delivering the at least one antidote into the body of the person are performed without intervention by the person or others.

30. The method according to claim 26, wherein the step of sending the second signal to the delivering means is manually performed by the person.

31. The method according to claim 18, further comprising measuring the density of the at least one antidote during the delivering step.

32. The method according to claim 18, further comprising sending a signal indicating the location of the person.

33. The method according to claim 18, further broadcasting an alert signal to a remote location if delivery of the at least one antidote is commenced.

34. The method according to claim 18, further comprising monitoring biological functions of the person, identifying biological information based on the biological functions, and sending the biological information to a remote location.

35. The method according to claim 18, wherein the detecting step comprises obtaining the fluid sample from the person's surroundings.

36. The method according to claim 35, wherein the fluid sample is air.

37. The method according to claim 35, wherein the fluid sample is water.

38. The method according to claim 18, wherein the detecting steps comprises detecting the type of the agent in the fluid sample.

39. The method according to claim 18, wherein the detecting step comprises detecting multiple different agents in the fluid sample and identifying multiple antidotes therefor to counteract the multiple different agents.

40. A method of detecting a chemical or biological agent and treating a person if the person is exposed to the agent, the method comprising the steps of:

equipping the person with a unit sufficiently small and light-weight to be carried by the person, the unit comprising at least one antidote for at least one agent selected from the group consisting of chemical and biological agents, means for selecting the at least one antidote, and means for delivering the at least one antidote into the body of the person;

detecting the presence of the at least one agent in a fluid sample near the person;

if the agent is detected, sending a first signal to the selecting means;

selecting with the selecting means the at least one antidote as being capable of counteracting the agent in accordance with the first signal;

sending a second signal to the delivering means; and then delivering with the delivering means the at least one antidote into the body of the person in response to the second signal;

wherein the step of delivering the at least one antidote comprises the steps of:

flowing the at least one antidote through a freestanding tube portion;

vibrating the freestanding tube portion at a resonant frequency thereof that varies with the density of the at least one antidote flowing therethrough, the Coriolis effect causing the freestanding tube portion to twist while being vibrated at resonance, the freestanding tube portion exhibiting a degree of twist that varies with the mass flow rate of the at least one antidote flowing therethrough;

sensing movement of the freestanding tube portion and producing a first output signal based on the resonant frequency of the freestanding tube portion and a second output signal based on the degree of twist of the freestanding tube portion;

measuring elapsed time during which the at least one antidote has flowed through the freestanding tube portion; and stopping flow of the at least one antidote through the freestanding tube portion in response to a specified amount of the at least one antidote having passed through the freestanding tube portion based on the elapsed time and the second output signal.

* * * * *